(12) United States Patent
Govari et al.

(10) Patent No.: US 12,239,447 B2
(45) Date of Patent: *Mar. 4, 2025

(54) MULTI-AXIAL POSITION SENSORS PRINTED ON A FOLDED FLEXIBLE CIRCUIT BOARD

(71) Applicant: Biosense Webster (Israel) Ltd., Yokneam (IL)

(72) Inventors: Assaf Govari, Haifa (IL); Meir Bar-Tal, Haifa (IL); Avi Reuveni, Givat Shmuel (IL)

(73) Assignee: Biosense Webster (Israel) Ltd. (IL)

( * ) Notice: Subject to any disclaimer, the term of this patent is extended or adjusted under 35 U.S.C. 154(b) by 203 days.

This patent is subject to a terminal disclaimer.

(21) Appl. No.: 17/690,051

(22) Filed: Mar. 9, 2022

(65) Prior Publication Data

US 2022/0265194 A1    Aug. 25, 2022

Related U.S. Application Data

(63) Continuation of application No. 15/433,072, filed on Feb. 15, 2017, now Pat. No. 11,304,642.

(51) Int. Cl.
*H01F 7/08* (2006.01)
*A61B 5/00* (2006.01)
(Continued)

(52) U.S. Cl.
CPC .............. *A61B 5/287* (2021.01); *A61B 5/062* (2013.01); *A61B 5/6851* (2013.01);
(Continued)

(58) Field of Classification Search
CPC ........ A61B 18/1492; A61B 2034/2051; A61B 34/20; A61B 5/06; A61B 5/062;
(Continued)

(56) References Cited

U.S. PATENT DOCUMENTS 5,270,656 A * 12/1993 Roberts ............ G01R 33/34061
335/282
5,391,199 A   2/1995 Ben-Haim
(Continued)

FOREIGN PATENT DOCUMENTS

JP    04-301581 A    10/1992
JP    2003-310570 A    11/2003
(Continued)

OTHER PUBLICATIONS

Chinese Office Action, the Frist Office Action and Search Report, dated Dec. 3, 2021, for Application No. CN 201810149303.8, 12 pgs.

(Continued)

*Primary Examiner* — Joseph A Stoklosa
*Assistant Examiner* — Brian M Antiskay
(74) *Attorney, Agent, or Firm* — Frost Brown Todd LLP

(57) ABSTRACT

A position sensor includes a flexible substrate formed into a three-dimensional (3D) shape. At least first and second field-sensing coils are formed in first and second respective layers of the flexible substrate, such that in the 3D shape the first and second field-sensing coils have first and second respective axes that are not parallel to one another.

20 Claims, 2 Drawing Sheets

(51) Int. Cl.

| | |
|---|---|
| *A61B 5/05* | (2021.01) |
| *A61B 5/06* | (2006.01) |
| *A61B 5/287* | (2021.01) |
| *A61B 18/14* | (2006.01) |
| *A61B 34/00* | (2016.01) |
| *H01F 5/00* | (2006.01) |
| *H01F 41/04* | (2006.01) |
| *A61B 18/00* | (2006.01) |
| *A61B 34/20* | (2016.01) |
| *H01F 17/00* | (2006.01) |
| *H05K 1/02* | (2006.01) |
| *H05K 1/16* | (2006.01) |

(52) U.S. Cl.
CPC ........ *A61B 5/6852* (2013.01); *A61B 18/1492* (2013.01); *A61B 34/00* (2016.02); *H01F 5/003* (2013.01); *H01F 41/041* (2013.01); *A61B 2018/00351* (2013.01); *A61B 2018/00577* (2013.01); *A61B 2034/2051* (2016.02); *A61B 2560/0468* (2013.01); *A61B 2562/0223* (2013.01); *A61B 2562/04* (2013.01); *A61B 2562/06* (2013.01); *A61B 2562/12* (2013.01); *A61B 2562/125* (2013.01); *A61B 2562/164* (2013.01); *A61B 2562/166* (2013.01); *H01F 2017/006* (2013.01); *H05K 1/028* (2013.01); *H05K 1/165* (2013.01); *H05K 2201/051* (2013.01)

(58) Field of Classification Search
CPC ........ A61B 5/0422; A61B 2018/00351; A61B 2090/378; A61B 5/065; A61B 5/6852; A61B 8/12; A61B 2034/2072
USPC ......... 600/372–393, 434, 508–509, 544–545
See application file for complete search history.

(56) References Cited

U.S. PATENT DOCUMENTS

| | | | |
|---|---|---|---|
| 5,722,401 A | 3/1998 | Pietroski et al. | |
| 5,926,020 A | 7/1999 | Samson | |
| 6,159,644 A | 12/2000 | Satoh et al. | |
| 6,201,387 B1* | 3/2001 | Govari ................ | G01B 7/30 324/207.17 |
| 6,239,724 B1 | 5/2001 | Doron et al. | |
| 6,253,770 B1* | 7/2001 | Acker ................ | A61B 5/06 128/899 |
| 6,332,089 B1 | 12/2001 | Acker et al. | |
| 6,484,118 B1 | 11/2002 | Govari | |
| 6,618,612 B1 | 9/2003 | Acker et al. | |
| 6,690,963 B2 | 2/2004 | Ben-Haim et al. | |
| 7,197,354 B2* | 3/2007 | Sobe ................ | A61B 5/06 600/407 |
| 7,301,332 B2 | 11/2007 | Govari et al. | |
| 8,504,133 B2 | 8/2013 | Kordis et al. | |
| 8,543,190 B2 | 9/2013 | Wasson et al. | |
| 9,037,213 B2* | 5/2015 | Roth ................ | G01R 33/028 600/410 |
| 9,095,685 B2 | 8/2015 | Sela et al. | |
| 10,588,543 B2* | 3/2020 | Bar-Tal ................ | A61B 5/0538 |
| 11,304,642 B2 | 4/2022 | Govari et al. | |
| 2002/0065455 A1 | 5/2002 | Ben-Haim et al. | |
| 2003/0120150 A1 | 6/2003 | Govari | |
| 2003/0187347 A1* | 10/2003 | Nevo ................ | A61B 5/415 600/424 |
| 2004/0068178 A1 | 4/2004 | Govari | |
| 2007/0219551 A1* | 9/2007 | Honour ................ | A61B 5/6852 606/41 |
| 2008/0140006 A1 | 6/2008 | Eskuri et al. | |
| 2010/0324412 A1* | 12/2010 | Govari ................ | A61B 34/20 600/424 |
| 2012/0172716 A1* | 7/2012 | Sela ................ | A61B 5/062 29/605 |
| 2013/0066194 A1 | 3/2013 | Seter et al. | |
| 2013/0169272 A1* | 7/2013 | Eichler ................ | A61B 90/37 324/253 |
| 2014/0276004 A1 | 9/2014 | Strupeck et al. | |

FOREIGN PATENT DOCUMENTS

| | | |
|---|---|---|
| JP | 2010-122012 A | 6/2010 |
| WO | 96/05768 A1 | 2/1996 |

OTHER PUBLICATIONS

Chinese Office Action, the Second Office Action and Supplemental Search Report, dated Sep. 5, 2022, for Application No. CN 201810149303.8, 14 pgs.
European Search Report and Written Opinion dated Jun. 28, 2018 for Application No. EP 18156795.9, 9 pgs.
European Examination Report dated Dec. 17, 2019 for Application No. EP 18156795.9, 7 pgs.
European Search Report, Extended, and Written Opinion, dated Jul. 5, 2021, for Application No. EP 21163765.7, 10 pgs.
European Search Report, Extended, and Written Opinion, dated Jul. 18, 2024 for Application No. EP 24173489.6, 12 pgs.
Japanese Office Action dated Dec. 7, 2021, for Application No. JP 2018-023791, 5 pgs.

* cited by examiner

MULTI-AXIAL POSITION SENSORS PRINTED ON A FOLDED FLEXIBLE CIRCUIT BOARD

This application is a continuation of U.S. patent application Ser. No. 15/433,072, filed Feb. 15, 2017, and issued as U.S. Pat. No. 11,304,642 on Apr. 19, 2022.

FIELD OF THE INVENTION

The present invention relates generally to medical instruments fitted with position sensors, and particularly to medical instruments in which coils of the position sensors are formed on flexible circuit boards.

BACKGROUND OF THE INVENTION

Medical instruments used in various medical applications, such as cardiac catheters, employ position sensors for determining the instrument location inside the body. A position sensor typically comprises multiple coils. Several implementations of such coils are known in the art.

For example, U.S. Pat. No. 8,504,133, whose disclosure is incorporated herein by reference, describes a system for sensing multiple local electrical voltages from endocardial surface of a heart. The system includes an elongate tubular member; a plurality of flexible splines having proximal portions, distal portions and medial portions therein between; an anchor for securely affixing the proximal portions of the splines; an atraumatic tip for securely affixing the distal portions of the splines; and a polymeric member including opposed a first open end and a second open end defining an open lumen therein between and an inner member surface and an outer member surface.

U.S. Pat. No. 5,722,401, whose disclosure is incorporated herein by reference, describes a catheter probe comprising a flexible elongate tubular member having proximal and distal extremities. An expandable assembly capable of moving from a contracted position to an expanded position is secured to the distal extremity of the flexible elongate tubular member and is formed from at least two elongate members movable between contracted and expanded positions.

SUMMARY OF THE INVENTION

An embodiment of the present invention that is described herein provides a position sensor including a flexible substrate formed into a three-dimensional (3D) shape. At least first and second field-sensing coils are formed in first and second respective layers of the flexible substrate, such that in the 3D shape the first and second field-sensing coils have first and second respective axes that are not parallel to one another.

In some embodiments, the flexible substrate includes a flexible circuit board. In other embodiments, the 3D shape includes a cylindrical shape. In yet other embodiments, the position sensor includes a third field-sensing coil that, in the 3D shape, has a third axis that is not parallel to any of the first and second axes. In an embodiment, the third field-sensing coil is formed on a third layer of the flexible substrate.

In another embodiment, the first and second layers are electrically isolated from one another. In yet another embodiment, in the 3D shape, the first and second axes are orthogonal to one another. In some embodiments, the position sensor includes one or more electrodes formed on a surface of the flexible substrate. In other embodiments, the first and second coils are configured to sense respective components of a magnetic field having different respective orientations, and to generate corresponding electrical signals indicative of the sensed components of the magnetic field. In yet other embodiments, the position sensor includes a ferromagnetic element, which is coupled to or adjacent to the flexible substrate and is configured to amplify at least one of the sensed components.

There is additionally provided, in accordance with an embodiment of the present invention, a method for producing a position sensor. The method includes forming at least first and second field-sensing coils in first and second respective layers of a flexible substrate, such that when the substrate is formed into a three-dimensional (3D) shape, the first and second field-sensing coils have first and second respective axes that are not parallel to one another. The flexible substrate are formed into the 3D shape.

The present invention will be more fully understood from the following detailed description of the embodiments thereof, taken together with the drawings in which:

DETAILED DESCRIPTION OF EMBODIMENTS

Overview

Medical instruments such as catheters are used in a variety of therapeutic and diagnostic medical procedures, such as, for example, in cardiac electrophysiological (EP) mapping and ablation. Catheter distal ends may comprise one or more position sensors. A position sensor may comprise multiple (e.g., three) coils arranged orthogonally to, and concentric with, one another, wound on a common form, and fitted into the distal end. The production of such coils, however, is relatively costly due to the mechanical winding of three coils. Furthermore, such a coil structure occupies valuable volume real estate in the catheter.

Embodiments of the present invention that are described hereinbelow provide improved methods for producing a position sensor, such as a triple-axis sensor (TAS) for medical probes, which overcome the above limitations. In some embodiments, the position sensor comprises a multi-layer flexible substrate, which is configured to be formed (e.g., folded or rolled) into a given three-dimensional (3D) shape, such as a cylindrical shape. The position sensor further comprises three field sensing coils, electrically isolated from one another, formed on three respective layers of the flexible substrate. When the substrate is formed into the given (e.g., cylindrical) shape, the axes of the three sensing coils are substantially orthogonal to one another.

In some embodiments, the substrate formed into the cylindrical shape has an overall diameter that fits into the distal end of the catheter. In an embodiment, the cylindrical shape is hollow, thereby enabling threading electrical conductors or tubes through the center of the cylindrical shape. Furthermore, the cylindrical shape may also serve as a structural component for mechanically strengthening the distal end of the catheter.

In some embodiments, each of the sensing coils is configured to sense a magnetic field at a dedicated orientation, and to generate a corresponding electrical signal indicative of the sensed respective magnetic field. The electrical signals may be used for estimating the location and orientation of the catheter distal end within a patient body. In an embodiment, the position sensor may further comprise a ferromagnetic element disposed on the flexible substrate, or in close proximity to the substrate, so as to increase the sensitivity of the position sensor by increasing the magnetic field amplitude sensed by the coils.

The disclosed techniques enable producing position sensors having multiple coils that substantially reduce the occupied volume within the distal end, and eliminate the need for mechanically winding the coils, so as to reduce the associated production costs. Furthermore, using the disclosed techniques enable customizing the shape of the position sensor so as to fit the space designated for the sensor in the distal end of the catheter.

System Description

Figure 1:
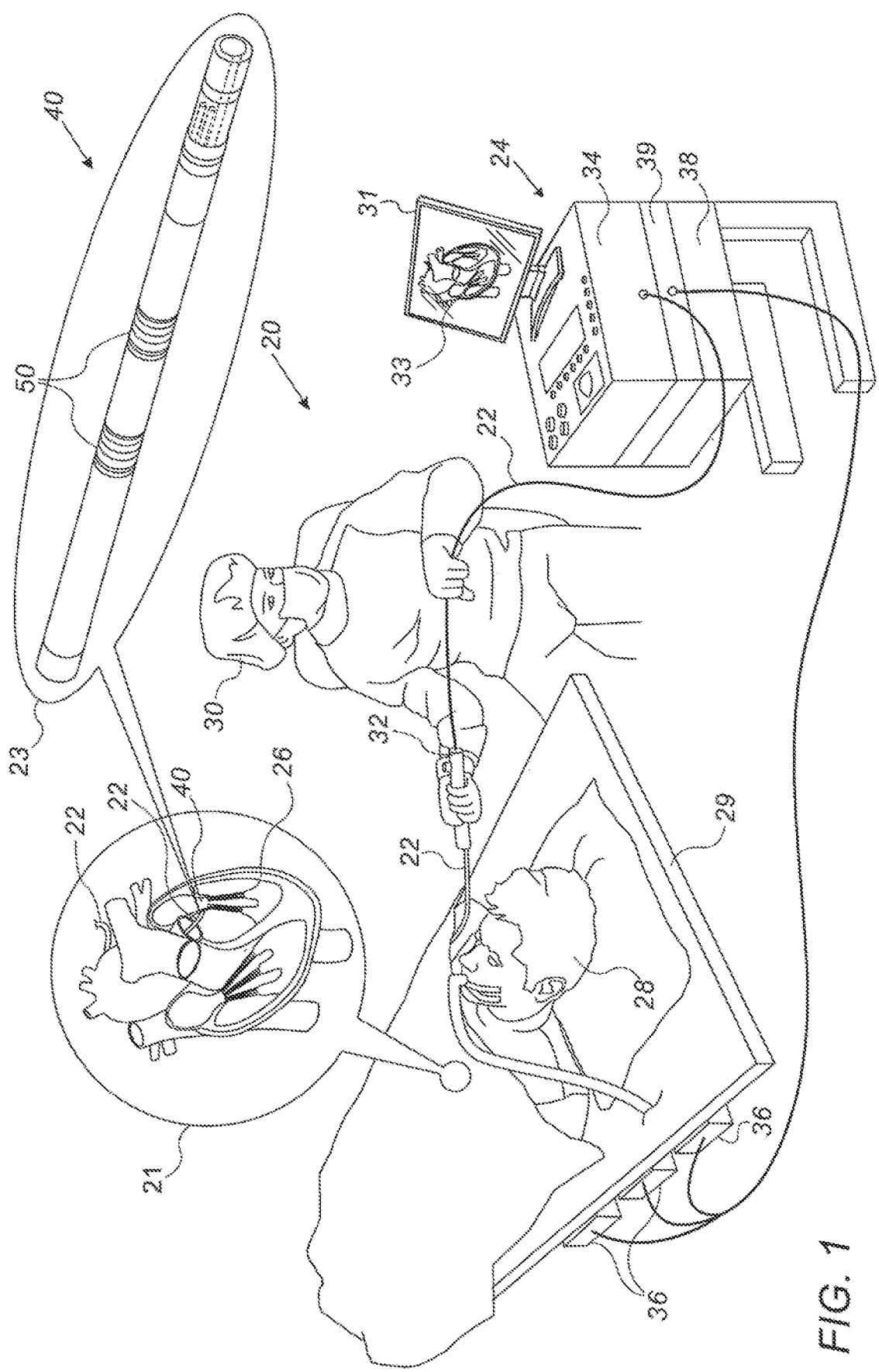
FIG. 1 is a schematic, pictorial illustration of a catheter tracking system, in accordance with an embodiment of the present invention.

FIG. 1 is a schematic, pictorial illustration of a catheter tracking system 20, in accordance with an embodiment of the present invention. System 20 comprises a probe 22, in the present example a cardiac catheter, and a control console 24. In the embodiment described herein, catheter 22 may be used for any suitable therapeutic and/or diagnostic purposes, such as ablation of tissue in a heart 26 and the mapping of electro-cardiac signals for the diagnosis of cardiac dysfunctions, such as cardiac arrhythmias, for example.

Console 24 comprises a processor 39, typically a general-purpose computer, with suitable front end and interface circuits for receiving signals from catheter 22 and for controlling the other components of system 20 described herein. Processor 39 may be programmed in software to carry out the functions that are used by the system, and the processor stores data for the software in a memory 38. The software may be downloaded to console 24 in electronic form, over a network, for example, or it may be provided on non-transitory tangible media, such as optical, magnetic or electronic memory media. Alternatively, some or all of the functions of processor may be carried out by dedicated or programmable digital hardware components.

An operator 30 (such as an interventional cardiologist) inserts catheter 22 through the vascular system of a patient 28 lying on a table 29. Catheter 22 comprises an insertion tube, and a distal-end assembly 40 that comprises one or more position sensors 50 shown in an inset 23. Operator 30 moves assembly 40 of catheter 22 in the vicinity of the target region in heart 26 by manipulating catheter 22 with a manipulator 32 near the proximal end of the catheter as shown in an inset 21. The proximal end of catheter 22 is connected to interface circuitry in processor 39.

The position of the distal-end assembly in the heart cavity is typically measured by magnetic position sensing in catheter tracking system 20. In this case, console 24 comprises a driver circuit 34, which drives magnetic field generators 36 placed at known positions external to patient 28 lying on table 29, e.g., below the patient's torso.

Reference is now made to inset 23. Distal-end assembly 40 typically comprises one or more position sensors 50 and, for example, one or more mapping electrodes (not shown). When the distal-end assembly is brought into contact with the inner heart surface, the mapping electrodes generate potential gradient signals in response to the sensed electrical potentials and position sensors 50 generate position signals in response to the sensed external magnetic fields, thereby enabling processor 39 to map the electrical potentials as a function of position within the heart cavity.

The multiple position sensors and mapping electrodes in assembly 40 are connected to interface circuitry in processor 39 at the catheter proximal end. Operator 30 can view the position of assembly 40 in an image 33 of heart 26 on a user display 31.

This method of position sensing is implemented, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Publication 2002/0065455 A1, issued as U.S. Pat. No. 6,690,963 on Jan. 10, 2004; U.S. Patent Publication 2003/0120150 A1, issued as U.S. Pat. No. 7,729,742 on Jun. 1, 2010; and U.S. Patent Publication 2004/0068178 A1, now abandoned, whose disclosures are all incorporated herein by reference.

Figure 2A:
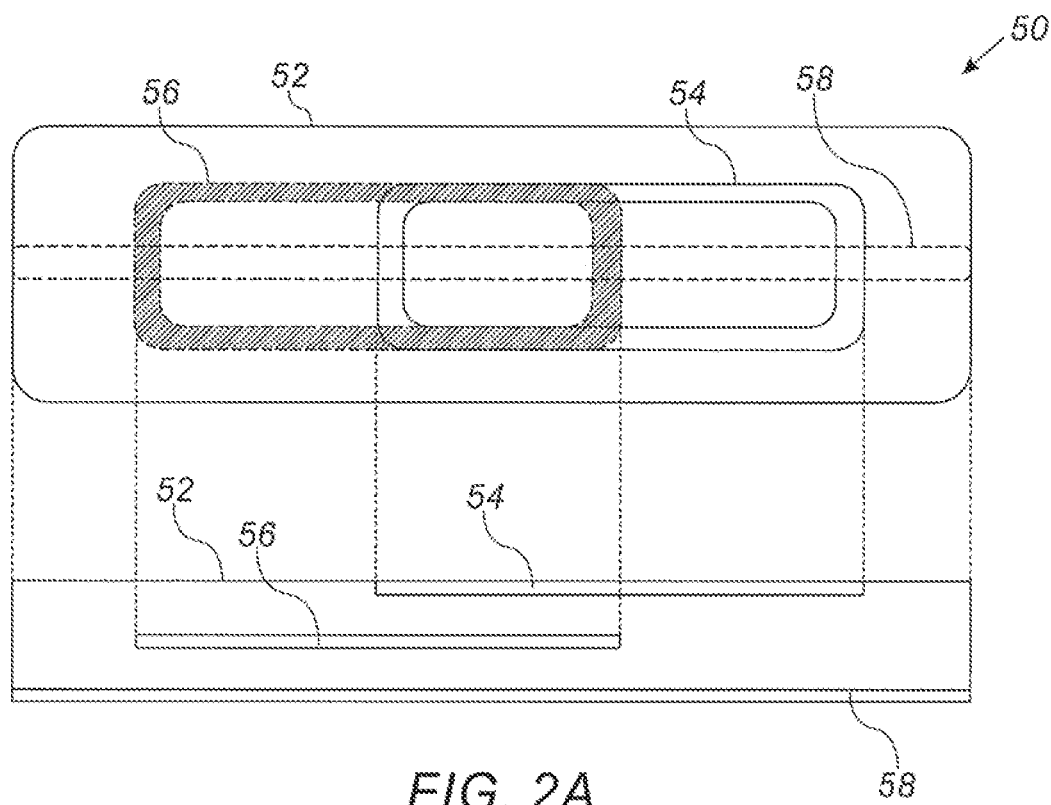
FIG. 2A is a schematic, pictorial illustration of a flexible substrate from which a position sensor is made, in an unfolded position, in accordance with an embodiment of the present invention.
Figure 2B:
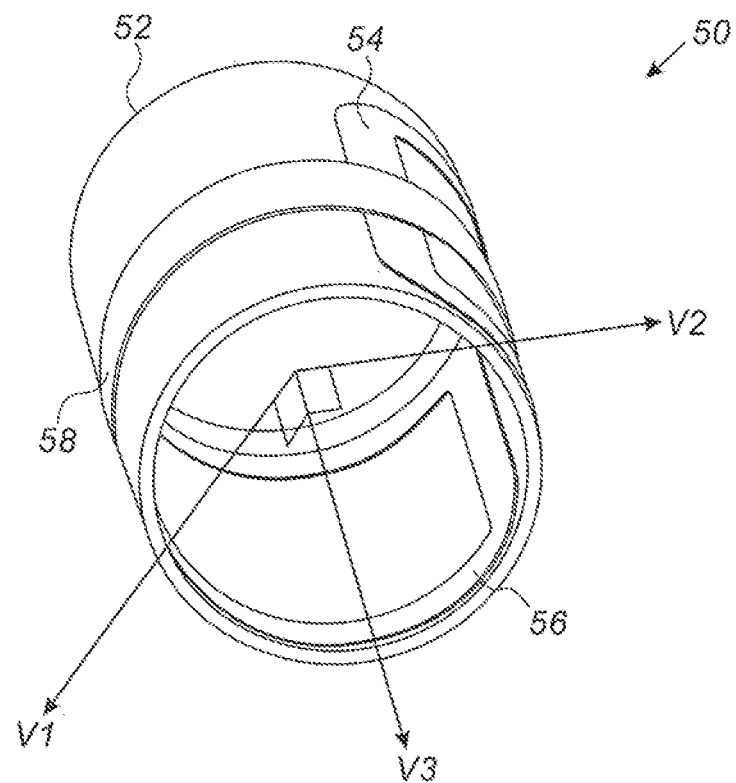
FIG. 2B is a schematic, pictorial illustration of a position sensor in a folded position, in accordance with an embodiment of the present invention.

A Position Sensor Disposed on a Flexible Substrate Formed into a Three-Dimensional (3D) Shape FIG. 2A is a schematic, pictorial illustration of a flexible substrate from which position sensor 50 is made, in accordance with an embodiment of the present invention. The position sensor that is formed by forming the substrate into a cylindrical shape is shown in FIG. 2B below. The upper part of FIG. 2A represents a top view, and the lower part of FIG. 2A represents a sectional side view, showing the structure of layers formed in the substrate.

In some embodiments, the substrate comprises a flexible circuit board 52 made from Kapton™ or any other suitable material. In some embodiments, one or more coils, such as coils 54, 56 and 58, are formed on or within layers of board 52. Coils 54, 56 and 58 are made from a conductive material, such as copper, and are formed on board 52 using any suitable production technique known in the art.

As shown in the sectional view of FIG. 2A, coil 54 is formed on the upper surface of board 52, coil 56 is embedded within an internal layer of board 52, and coil 58 is formed on the lower surface of board 52, which is the external surface of board 52 that faces the tissue after rolling the board. In this arrangement, coils 54, 56 and 58 are electrically isolated from one another by suitable dielectric layers.

In an embodiment, each of coils 54, 56 has a substantially symmetrical shape. In the example of FIG. 2A, each of coils 54 and 56 has a rectangular closed-loop shape, but may alternatively have any other suitable shape. In an embodiment, coil 58 comprises a stripe that passes end-to-end along the board 52. In some embodiments, each of coils 54, 56, and 58 is electrically connected to catheter 22 via electrical circuit traces (not shown) printed on board 52.

FIG. 2B is a schematic, pictorial illustration of position sensor 50 in a folded position, in accordance with an embodiment of the present invention. In some embodiments, in folded board 52, axes V1, V2 and V3 of respective coils 54, 56 and 58, are substantially orthogonal to one another. As can be seen in FIG. 2A above, coils 54 and 56 are formed with a certain offset relative to one another on board 52. The offset is calculated so that, after board 52 is rolled to the cylindrical shape, the two coils will be oriented with mutually-orthogonal axes.

In the example of FIG. 2B, board 52 is rolled to form a cylindrical shape having a diameter of 2 mm or any other suitable size that may fit in distal end 40. In an embodiment, the left and right edges of coil 58 are coupled to one another so that coil 58 also formed a symmetrical loop along the circumference of the cylinder.

In an embodiment, board 52 formed into the cylindrical shape may be used as a structural component that mechanically strengthens the wall of distal end 40. In some embodiments, the hollowed-shaped cylinder enables threading electrical conductors, tubes or other elements through the center of the cylindrical shape.

In some embodiments, in the presence of magnetic fields generated by generators 36, each of coils 54, 56, and 58, senses a magnetic field at a different orientation (depending on the axes V1, V2 and V3), and generates a respective electrical signal indicative of the respective sensed field. The electrical signals produced by coils 54, 56, and 58 are transmitted, via assembly 40, to processor 39, which is configured to estimate the position of assembly 40 in heart 26, based on the electrical signals.

In some embodiments, sensor 50 may further comprise a ferromagnetic element (not shown) located at distal end 40, in close proximity to coils 54, 56, and 58. The ferromagnetic element is configured to amplify the magnetic field sensed by coils 54, 56, and 58, thereby increasing the sensitivity of sensor 50 to the magnetic fields produced by generators 36.

In an embodiment, the ferromagnetic element may be formed on board 52, for example, as a separate layer. In another embodiment, the ferromagnetic element may be disposed in close proximity to board 52, for example, at the center of the volume within the cylindrical shape of board 52 (e.g., at intersection point of the axes V1, V2, and V3 in FIG. 2B). The size, shape, position within distal end 40, and magnetic characteristics of the ferromagnetic element may determine the sensitivity of sensor 52 and the number of coils to be formed so as to produce the electrical signal indicative of the sensed magnetic field.

In an embodiment, sensor 50 may further comprise one or more electrodes (not shown), such as ablation electrodes or electropotential (EP) sensors, formed on the external surface of board 52 that faces the tissue after rolling the board. In an embodiment, the electrodes may be electrically connected to catheter 22 via electrical circuit traces (not shown) printed on board 52.

In an embodiment, the cylindrical shape of board 52 forms a triple axes sensor (TAS) by forming coils 54, 56, and 58 substantially orthogonal to one another, as demonstrated by orthogonal axes V1, V2 and V3 in the figure.

In other embodiments, sensor 50 may comprise only two coils (not shown). For example, coil 54 may be formed on the upper surface of board 52, coil 56 may be formed on the external surface of board 52 that faces the tissue after rolling the board, and coil 58 is omitted. In this embodiment, by forming board 52 into a cylindrical shape, sensor 50 becomes a dual-axis sensor. In an embodiment, coil 58 may be formed on a separate stripe of metal, e.g., on a separate flexible board (not shown), which is formed into a cylindrical shape and coupled to board 52 (e.g., wrapped around or wrapped within) at any suitable configuration. In this arrangement coils 54, 56, and 58 are further connected to catheter 22 (e.g., using electrical circuit traces as described in FIG. 2A above) so as to enable a TAS having substantially similar functionality of the configuration depicted in FIG. 2B. In an embodiment, one or more electrodes, such as ablation electrodes or electropotential (EP) sensors, may be formed on the separate flexible board, in addition to coil 58.

The configurations of coils 54, 56, and 58, and the cylindrical shape of folded board 52 shown in FIGS. 2A and 2B are depicted purely by way of example. In alternative embodiments, sensor 50 may comprise any suitable number of coils, having any suitable shape and arranged so that board 52 may be folded into any suitable shape, thereby arranging the axes of the coils at any angle that is not parallel with one another.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A position sensor, comprising:
   (a) a flexible substrate defining a central longitudinal axis;
   (b) a first field-sensing coil formed on a first layer of the flexible substrate, the field-sensing coil defining a closed-loop shape that fully encircles a first axis, the first axis being orthogonal to the central longitudinal axis; and
   (c) a second field-sensing coil formed on a second layer of the flexible substrate, the second field-sensing coil defining a closed-loop shape that fully encircles the central longitudinal axis, the second field-sensing coil overlappingly wraps around the first field-sensing coil at a common longitudinal position along the central longitudinal axis.

2. The position sensor of claim 1, the first field-sensing coil being configured to sense components of a magnetic field oriented about the first axis.

3. The position sensor of claim 1, the second field-sensing coil being configured to sense components of a magnetic field oriented about the central longitudinal axis.

4. The position sensor of claim 1, the flexible substrate forming a cylindrical shape extending along the central longitudinal axis.

5. The position sensor of claim 1, further comprising a third field-sensing coil.

6. The position sensor of claim 5, the third field-sensing coil sharing the common longitudinal position along the central longitudinal axis.

7. The position sensor of claim 6, the third field-sensing coil being formed on a third layer of the flexible substrate.

8. A position sensor, comprising:
   (a) a flexible substrate formed into a three-dimensioned object defining an opening extending along a central longitudinal axis;
   (b) a first field-sensing coil formed on a first layer of the flexible substrate, the first field sensing coil defining a closed-loop shape that fully encircles a first axis, the first axis being orthogonal to the central longitudinal axis; and (c) a second field-sensing coil formed on a second layer of the flexible substrate, the second field-sensing coil defining a closed-loop shape that fully encircles a second axis, the second axis being orthogonal to both the central longitudinal axis and the first axis, the first field-sensing coil and the second field-sensing coil being located at a common longitudinal location, the first field-sensing coil and the second field-sensing coil being configured to sense components of a magnetic field oriented along the first axis and the second axis, respectively.

9. The position sensor of claim 8, the first field-sensing coil further comprising a rectangular-shape defining the closed-loop shape.

10. The position sensor of claim 8, the second field-sensing coil further comprising a rectangular-shape defining the closed-loop shape.

11. The position sensor of claim 8, the flexible substrate comprising a flexible circuit board.

12. The position sensor of claim 8, the first field-sensing coil comprising a conductive material.

13. The position sensor of claim 12, the conductive material comprising a copper material.

14. The position sensor of claim 8, the first field-sensing coil being located adjacent to a top surface of the flexible substrate.

15. The position sensor of claim 14, the second field-sensing coil being located adjacent to a bottom surface of the flexible substrate.

16. A position sensor, comprising:
(a) a flexible substrate bent into a three-dimensioned shape defining an opening extending along a central axis;
(b) a first field-sensing coil fixed to a first layer of the flexible substrate, the first field-sensing coil forming a closed-loop shape that encompasses a first axis being orthogonal to the central axis;
(c) a second field-sensing coil fixed to a second layer of the flexible substrate, the second layer being offset from the first layer, the second field sending field-sensing coil forming a closed-loop shape that encompasses a second axis that is orthogonal to the central axis; and
(d) a third field-sensing coil fixed to a third layer of the flexible substrate, the third layer being offset from the first layer and the second layer such that the first field-sensing coil, the second field-sensing coil, and the third field-sensing coil are electrically isolated relative to each other, the third field-sensing coil forming a closed-loop shape that encompasses the central axis and further overlappingly wraps around the first and second field-sensing coils.

17. The position sensor of claim 16, the first axis and the second axis being orthogonal relative to each other.

18. The position sensor of claim 16, the first field-sensing coil and the second field sensing coil extending along a common longitudinal section of the flexible substrate.

19. The position sensor of claim 18, the third field-sensing coil being located within the common longitudinal section.

20. The position sensor of claim 16, the three-dimensioned shape comprising a hollow cylinder.

* * * * *